US011199289B2

(12) United States Patent
Lorenz et al.

(10) Patent No.: US 11,199,289 B2
(45) Date of Patent: Dec. 14, 2021

(54) APPARATUS, SURGICAL MICROSCOPY SYSTEM, AND METHOD FOR COMPENSATING A BALANCING ERROR IN A STAND FOR A SURGICAL MICROSCOPE

(71) Applicant: Carl Zeiss Meditec AG, Jena (DE)

(72) Inventors: Axel Lorenz, Meißen (DE); Florian Bart, Aalen (DE); Wolfgang Kircher, Heidenheim (DE)

(73) Assignee: Carl Zeiss Meditec AG, Jena (DE)

(*) Notice: Subject to any disclaimer, the term of this patent is extended or adjusted under 35 U.S.C. 154(b) by 168 days.

(21) Appl. No.: 16/575,062

(22) Filed: Sep. 18, 2019

(65) Prior Publication Data

US 2021/0080046 A1 Mar. 18, 2021

(51) Int. Cl.
*F16M 11/12* (2006.01)
*F16M 11/18* (2006.01)
*A61B 90/25* (2016.01)

(52) U.S. Cl.
CPC ............ *F16M 11/12* (2013.01); *A61B 90/25* (2016.02); *F16M 11/18* (2013.01); *F16M 2200/041* (2013.01); *F16M 2200/063* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,891,301 A | * | 6/1975 | Heller | G02B 7/001 359/384 |
| 4,344,595 A | * | 8/1982 | Heller | F16M 11/2035 248/542 |
| 5,205,522 A | * | 4/1993 | Nakamura | F16M 11/043 248/123.11 |
| 5,383,637 A | * | 1/1995 | Biber | F16M 11/10 248/291.1 |
| 6,105,909 A | * | 8/2000 | Wirth | A61B 90/25 248/123.2 |
| 6,543,914 B2 | * | 4/2003 | Sander | F16M 11/08 362/401 |
| 6,871,828 B2 | | 3/2005 | Frick et al. | |
| 7,128,300 B2 | * | 10/2006 | Frick | F16M 11/2014 248/418 |

(Continued)

FOREIGN PATENT DOCUMENTS

DE 102016200213 A1 7/2017

*Primary Examiner* — Monica E Millner
(74) *Attorney, Agent, or Firm* — Falk Ewers; Ewers IP Law PLLC (57) ABSTRACT

A stand for a surgical microscope includes a first stand part including a first bearing and a second bearing, a shaft arranged in the first bearing and defining a rotation axis, a second stand part fixedly connected to the shaft, mounted on the first stand part together with the shaft pivotably about the rotation axis, and including a force transmission point, a lever part mounted on the second stand part at the force transmission point, arranged pivotably about the rotation axis, and including a third bearing, and a torque compensation assembly applying a counter torque to the second stand part to compensate a load torque including a dynamic load torque occurring when the second stand part is pivoted about the rotation axis and a static load torque resulting from a gravitation force acting on the second stand part and on elements mounted on the second stand part.

19 Claims, 8 Drawing Sheets

(56) References Cited

U.S. PATENT DOCUMENTS

| | | | |
|---|---|---|---|
| 7,798,035 B2 | 9/2010 | Duval | |
| 8,205,845 B2* | 6/2012 | Hammer | F16M 11/2092 248/276.1 |
| 8,448,909 B2* | 5/2013 | Metelski | A61B 90/25 248/281.11 |
| 9,885,858 B2* | 2/2018 | Ernsperger | G02B 21/365 |
| 2002/0185583 A1* | 12/2002 | Metelski | G02B 7/001 248/676 |
| 2007/0012853 A1* | 1/2007 | Strauss | F16M 11/2071 248/648 |
| 2009/0218455 A1 | 9/2009 | Metelski | |
| 2013/0327902 A1 | 12/2013 | Frick et al. | |
| 2017/0198856 A1* | 7/2017 | Voigt | F16M 11/42 |
| 2018/0110581 A1* | 4/2018 | Kamata | G02B 7/001 |
| 2018/0168767 A1* | 6/2018 | Hirose | G02B 21/24 |
| 2019/0250360 A1* | 8/2019 | Liu | A61B 90/50 |
| 2021/0077218 A1* | 3/2021 | Lorenz | G02B 21/24 |
| 2021/0093411 A1* | 4/2021 | Hirose | G02B 7/001 |

* cited by examiner

Related Art

APPARATUS, SURGICAL MICROSCOPY SYSTEM, AND METHOD FOR COMPENSATING A BALANCING ERROR IN A STAND FOR A SURGICAL MICROSCOPE

TECHNICAL FIELD

The invention relates to a stand for a surgical microscope, a surgical microscopy system, and a method for compensating a balancing error in a stand for a surgical microscope.

BACKGROUND

A surgical microscope for installation on the floor in the middle price segment (midrange) typically includes a stand, a microscope head, and a suspension mechanism for mounting the microscope head on the stand. The suspension mechanism can be, e.g., a yoke.

These surgical microscopes are typically used in the field of neurosurgery or otolaryngology. Some stands for surgical microscopes have a Selective Compliance Assembly Robot Arm (SCARA) design, i.e., the stands have two parallel vertical axes and associated support arms which allow positioning of the microscope head in a horizontal plane.

If one of the support arms has a parallel kinematics (also referred to as carrier arm or boom arm) in the vertical plane, the degree of freedom is extended by the stroke range so that a spatial positioning of the microscope head is possible while maintaining the orientation of the microscopy head.

In order to permit a smooth, near-force-free movement of the microscope head in a vertical direction, the carrier arm needs not only to provide a suspension mechanism for mounting the microscope head on the carrier arm, but also a load and angle-dependent weight compensation mechanism.

In addition, a SCARA support arm, and in particular the carrier arm, always represents a disturbance contour in the field of view. On the one hand, direct eye contact in the surgery room is disturbed as well as the field of view of all participants in the surgery on assistance devices or imaging devices. In addition, especially in microsurgery, the microscope head often has to be swiveled away or swiveled upwards during the surgery in order to allow access for other devices, e.g., mobile X-ray machines.

Since the per se non-sterile carrier arm protrudes for the most part into the sterile working area and is typically only partially draped, it needs to be avoided that the sterile surgical personnel gets in contact with the non-sterile carrier arm.

Especially in the surgery room, where doctor(s) and assistant(s) operate in positions facing each other, i.e., in positions on opposite sides of a patient (which is possible, e.g., by utilizing an optical beam divider (stereo bridge) and 2 tubes on the microscope head), at least one person must stand directly under the carrier arm. Therefore, a certain free space between the carrier arm and the head of the person standing directly under the carrier arm needs to always be provided. This free space is referred to hereinafter as overhead clearance (OC).

Furthermore, parts attached to the carrier arm or backpack-like housing parts typically provided to cover mechanical parts which are moved when the carrier arm is swiveled disturb the field of view in the working environment of all participants in the surgery and may also lead to system-related collisions.

For the reasons discussed above, while the carrier arm must have a sufficient stiffness and a necessary strength, the carrier arm must also be inconspicuous and compact in its appearance. However, existing stands for surgical microscope systems require a large space for the balancing mechanism.

An ideal mechanical balancing mechanism with a compression spring (provided as a swivel spring) for tensile force recognition, which shows an uncritical failure behavior due to the system in the event of a fault, is described, e.g., in DE 10 2016 200 213 A1. The space required by the swivel spring itself for a typically required swivel range of the carrier arm of approximately 50° to 70° around a swivel axis of the carrier arm is very large and leads to massive interference geometries due to the required covers for the swivel spring. In addition, the mechanical balancing mechanism described in DE 10 2016 200 213 A1 cannot handle variations of the load because this would require structural changes in the mechanics of the balancing mechanism.

As a result, there has been a continuing need for a stand for a surgical microscope that has a significantly reduced disturbing geometry and an increased and guaranteed overhead clearance for personnel standing under the carrier arm.

SUMMARY

It is therefore an object of the present invention to improve the geometry of a stand for a surgical microscope and of a surgical microscopy system, and the overhead clearance of a carrier arm of the stand for the surgical microscope.

This object is achieved by a stand for a surgical microscope including a first stand part having a first bearing and a second bearing, a shaft arranged in the first bearing and defining a rotation axis, a second stand part fixedly connected to the shaft, mounted on the first stand part together with the shaft pivotably about the rotation axis, and including a force transmission point, a lever part mounted on the second stand part at the force transmission point, arranged pivotably about the rotation axis, and including a third bearing, a torque compensation assembly applying a counter torque to the second stand part to compensate a load torque including a dynamic load torque occurring when the second stand part is pivoted about the rotation axis and a static load torque resulting from a gravitation force acting on the second stand part and on elements mounted on the second stand part.

According to an aspect of the disclosure, the torque compensation assembly includes a first torque compensation assembly and a second torque compensation assembly. The rotation axis is a first rotation axis. The second bearing defines a second rotation axis. The first torque compensation assembly is mounted on the first stand part in the second bearing and is pivotable about the second rotation axis within a first swivel range.

The first torque compensation assembly includes a rod which is displaceable relative to the first stand part and which is mounted on the lever part in the third bearing. The second torque compensation assembly is fixedly mounted on the shaft.

The counter torque includes a first portion and a second portion. The first torque compensation assembly applies the first portion of the counter torque to the second stand part thereby partially counteracting the load torque. The third bearing is arranged on the lever part at a position relative to the first bearing at which the first swivel range is a minimum swivel range thereby causing a balancing error preventing the first portion of the counter torque to cancel out the load torque. The second torque compensation assembly applies the second portion of the counter torque to the second stand part, and the second portion of the counter torque compensates the balancing error and an offset between different loads, i.e., deviations of the static load torque.

The balancing error varies depending on a rotation angle between the first stand part and the second stand part when the second stand part is pivoted about the first rotation axis and depending on a weight of objects mounted on the second stand part. The rotation angle can be converted into height over ground via trigonometric functions.

According to an aspect of the disclosure, the objects mounted on the second stand part include a surgical microscope head and a suspension mechanism.

According to another aspect of the disclosure, the first torque compensation assembly pivots within the minimum swivel range between zero degrees and five degrees.

According to yet another aspect of the disclosure, the first torque compensation assembly is a compression spring and the second torque compensation assembly is an electrical motor or an electrical motor with a gear.

The electrical motor may include a motor shaft, and the motor shaft may be mounted on the shaft by a coupling mechanism.

The stand may further have a connection element including a fourth bearing and a fifth bearing. The second stand part may include a main support arm and a secondary support arm. The first stand part may include a sixth bearing, and the main support arm may be pivotably mounted on the connection element in the fifth bearing. The secondary support arm may be pivotably mounted on the first stand part in the sixth bearing and on the connection element in the fourth bearing to compensate a tilting torque occurring on the connection element.

According to an aspect of the disclosure, the secondary support arm is arranged inside the main support arm, and each of the main support arm and the secondary support arm has a curved shape.

The first, fourth, fifth, and sixth bearings form a parallelogram, the parallelogram defines a second swivel range within which the second stand part is pivotable about the rotation axis, and the second swivel range is between zero degrees and sixty degrees.

The object is also achieved by a surgical microscopy system having a stand. The stand includes a first stand part having a first bearing and a second bearing, a shaft arranged in the first bearing and defining a rotation axis. A second stand part is fixedly connected to the shaft, mounted on the first stand part together with the shaft pivotably about the rotation axis. The second stand part includes a force transmission point. The surgical microscopy system further includes a lever part mounted on the second stand part at the force transmission point, arranged pivotably about the rotation axis, and including a third bearing, a torque compensation assembly applying a counter torque to the second stand part to compensate a load torque, a connection element including a fourth bearing and a fifth bearing. In addition, the second stand part includes a main support arm and a secondary support arm, and a sixth bearing. The secondary support arm being pivotably mounted on the second stand part in the sixth bearing and on the connection element in the fourth bearing. The main support arm is pivotably mounted on the connection element in the fifth bearing.

The surgical microscopy system further includes a surgical microscope head mounted on the connection element via a suspension mechanism. The load torque occurs when the second stand part is pivoted together with the surgical microscope head about the rotation axis.

According to an aspect of the disclosure, the secondary support arm is arranged inside the main support arm, each of the main support arm and the secondary support arm has a curved shape, and the curved shape of the main support arm and the secondary support arm provides an overhead clearance between the second stand part and a head of a person standing underneath the second stand part of at least 100 millimeters.

According to another aspect of the disclosure, the torque compensation assembly includes a first torque compensation assembly and a second torque compensation assembly, the rotation axis is a first rotation axis, the second bearing defines a second rotation axis, the first torque compensation assembly is mounted on the first stand part in the second bearing pivotably about the second rotation axis within a first swivel range. In addition, the first torque compensation assembly includes a rod displaceable relative to the first stand part and mounted on the lever part in the third bearing. The second torque compensation assembly is fixedly mounted on the shaft.

According to yet another aspect of the disclosure, the counter torque includes a first portion and a second portion, the first torque compensation assembly applies the first portion of the counter torque to the second stand part thereby partially counteracting the load torque, the third bearing is arranged on the lever part at a position relative to the first bearing at which the first swivel range is a minimum swivel range thereby causing a balancing error preventing the first portion of the counter torque to cancel out the load torque, the second torque compensation assembly applies the second portion of the counter torque to the second stand part, and the second portion of the counter torque compensates the balancing error and an offset between different loads, i.e., deviations of the static load torque.

According to a further aspect of the disclosure, the balancing error varies depending on a rotation angle between the first stand part and the second stand part when the second stand part is pivoted about the first rotation axis and depending on a weight of objects mounted on the second stand part.

According to another aspect of the disclosure, the objects mounted on the second stand part include the surgical microscope head and a suspension mechanism.

The object is further achieved by a method for compensating a balancing error in a stand of a surgical microscope. The method includes providing a first stand part, a second stand part, a lever part, and a torque compensation assembly, the torque compensation assembly including a first torque compensation assembly and a second torque compensation assembly, fixedly mounting the lever part on the second stand part, mounting the first torque compensation assembly pivotably within a first swivel range on the first stand part, mounting the second stand part pivotably within a second swivel range on the first stand part, applying a counter torque to the second stand part to compensate a load torque occurring when the second stand part is pivoted relative to the first stand part, the counter torque including a first portion and a second portion, the first portion being applied by the first torque compensation assembly and the second portion being applied by the second torque compensation assembly, mounting the first torque compensation assembly on the lever part at a position at which the first swivel range is a minimum swivel range thereby causing the balancing error preventing the first portion of the counter torque to cancel out the load torque, and compensating the balancing error by the second portion of the counter torque.

According to an aspect of the disclosure, the method further includes pivoting the first torque compensation assembly within the minimum swivel range between zero degrees and five degrees.

BRIEF DESCRIPTION OF THE DRAWINGS

The invention will now be described with reference to the drawings wherein.

DESCRIPTION OF EXEMPLARY EMBODIMENTS

Exemplary embodiments of the disclosure will be explained below with reference to the accompanying schematic figures. Features that coincide in their nature and/or function may in this case be provided with the same designations throughout the figures.

The terms "exhibit", "have", "comprise" or "include" or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B", "A has B", "A comprises B" or "A includes B" may refer both to the situation in which no further element aside from B is provided in A (that is to say to a situation in which A is composed exclusively of B) and to the situation in which, in addition to B, one or more further elements are provided in A, for example element C, elements C and D, or even further elements.

Furthermore, the terms "at least one" and "one or more" and grammatical modifications of these terms or similar terms, if they are used in association with one or more elements or features and are intended to express the fact that the element or feature can be provided singly or multiply, in general are used only once, for example when the feature or element is introduced for the first time. When the feature or element is subsequently mentioned again, the corresponding term "at least one" or "one or more" is generally no longer used, without restriction of the possibility that the feature or element can be provided singly or multiply.

Also, the terms "preferably", "in particular", "by way of example" or similar terms are used in conjunction with optional features, without alternative embodiments thereby being restricted. In this regard, features introduced by these terms are optional features, and there is no intention to restrict the scope of protection of the claims, and in particular of the independent claims, by these features. In this regard, the invention, as will be recognized by a person of ordinary skill in the art, can also be carried out using other configurations. Similarly, features introduced by "in one embodiment of the invention" or "in one exemplary embodiment of the invention" are to be understood to be optional features, without this being intended to restrict alternative refinements or the scope of protection of the independent claims. Furthermore, all possibilities of combining the features introduced by these introductory expressions with other features, whether optional or non-optional features, are intended to remain unaffected by said introductory expressions.

Figure 1:
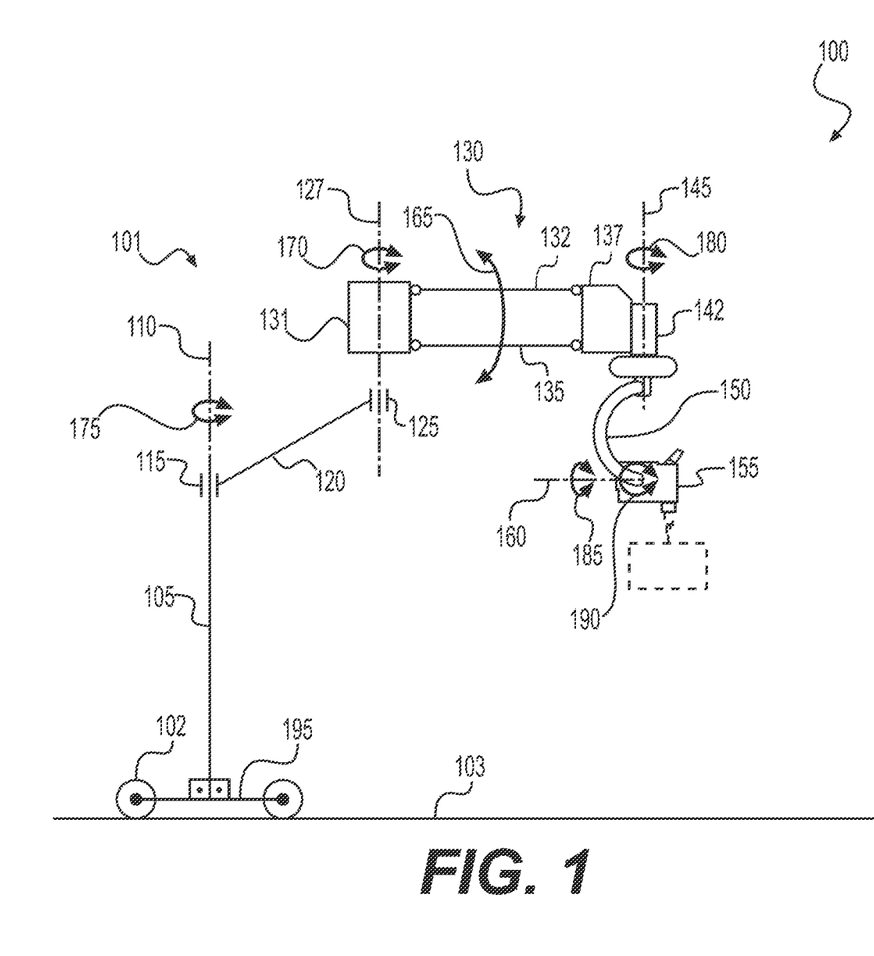
FIG. 1 shows a schematic illustration of surgical microscopy system according to an exemplary embodiment of the invention.

FIG. 1 shows device 1 a schematic illustration of surgical microscopy system 100. The surgical microscopy system 100 includes stand 101 and a microscope head 155. Stand 101 has a base part 195, a stand part 105, a first carrier arm 120, and a second carrier arm 130. The second carrier arm 130 has a first carrier arm part 132 and a second carrier arm part 135 forming a parallel kinematics.

The stand 101 further includes a connection element 137 on which the first carrier arm part 132 and the second carrier arm part 135 are pivotably mounted. The microscope head 155 is also mounted on the connection element 137 via a suspension mechanism which includes connection element 142 and yoke 150.

As shown in FIG. 1, the base part 195 has rollers 102 to move the surgical microscopy system 100 to a designated position in the operating theatre. At the designated position, the rollers are locked such that during normal operation, i.e., during a surgery, the stand 101 (and thereby the entire surgical microscopy system 100) is immovably fixed on the floor 103.

As shown in FIG. 1, the stand part 105 is fixedly mounted on the base part 195 and defines a first vertical axis 110. The first carrier arm 120 has bearings 115 and 125 and is mounted in bearing 115 pivotably about the first axis 110 on the stand part 105, as indicated by arrows 175. The bearing 125 defines a second vertical axis 127 which is parallel to the first vertical axis 110. The second carrier arm 130 includes a part 131 which is mounted pivotably about the second vertical axis 110 on the first carrier arm 120, as indicated by arrows 170.

By pivoting the first carrier arm 120 and the second carrier arm 130 about the first vertical axis 110 and the second vertical axis 127, respectively, the microscope head 155 can be moved in a horizontal plane. In addition, the first carrier arm part 132 and the second carrier arm part 135 of the second carrier arm 130 which form the parallel kinematics are pivotable in the vertical plane about a third axis, as indicated by arrows 165, thereby providing a degree of freedom which allows a spatial positioning of the microscope head 155 in all three directions of a coordinate system while maintaining the orientation of the microscopy head 155.

In addition, connection element 142 and yoke 150 of the suspension mechanism may include further bearings which allow the microscopy head 155 to be pivoted about a fourth axis 145 as indicated by arrows 180, about a fifth axis 160, as indicated by arrows 185, and about a sixth axis as indicated by arrows 190.

Figure 2:
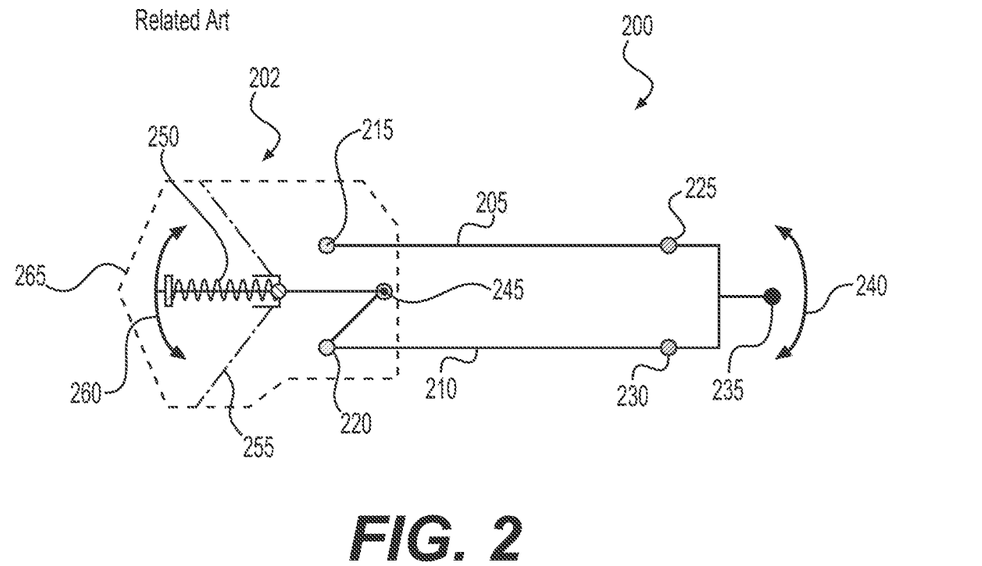
FIG. 2 shows a schematic illustration of a carrier arm and a balancing mechanism according to the related art.

FIG. 2 shows a schematic illustration of a carrier arm 200 known from the related art. The carrier arm 200 is in a middle position, i.e., in a position in which the carrier arm extends essentially parallel to a floor (not shown). The carrier arm 200 includes a first carrier arm part 205 having a first connecting point 215 and a second connecting point 225, and a second carrier arm part 210 having a third connecting point 220 and a fourth connecting point 230, which together form a parallel kinematics. A load (such as a microscope head) can be mounted at load mounting point 235 via a suspension mechanism (not shown).

The first carrier arm part 205 is pivotable about the first connecting point 215 and the second carrier arm part 210 is pivotable about the third connecting point 220, thereby allowing the carrier arm 200 to be vertically swiveled together with the load mounted at the load mounting point 235, as indicated by arrows 240.

The carrier arm 200 includes a balancing mechanism 202. The balancing mechanism 202 includes a spring 250 which is mounted on the second carrier arm part 210 at a connecting point 245, which pivots about a spring pivoting axis, as indicated by arrows 260, and which is covered by cover 265. The connecting point 245 is chosen to permit an optimal compensation of a load torque by the spring 250. Such a balancing mechanism is described in DE 10 2016 200 213 A1.

Because of the position of the connecting point 245 of the spring 250, the spring 250 has a large swivel range 255. For example, if the carrier arm 200 is swiveled between an upper swivel position and a lower swivel position in a swivel range between zero degrees and sixty degrees, the spring 250 has also a swivel range 255 between zero and sixty degrees. This large swivel range 255 of the spring 250 results in the cover 265 having a large disturbance contour.

Figure 3:
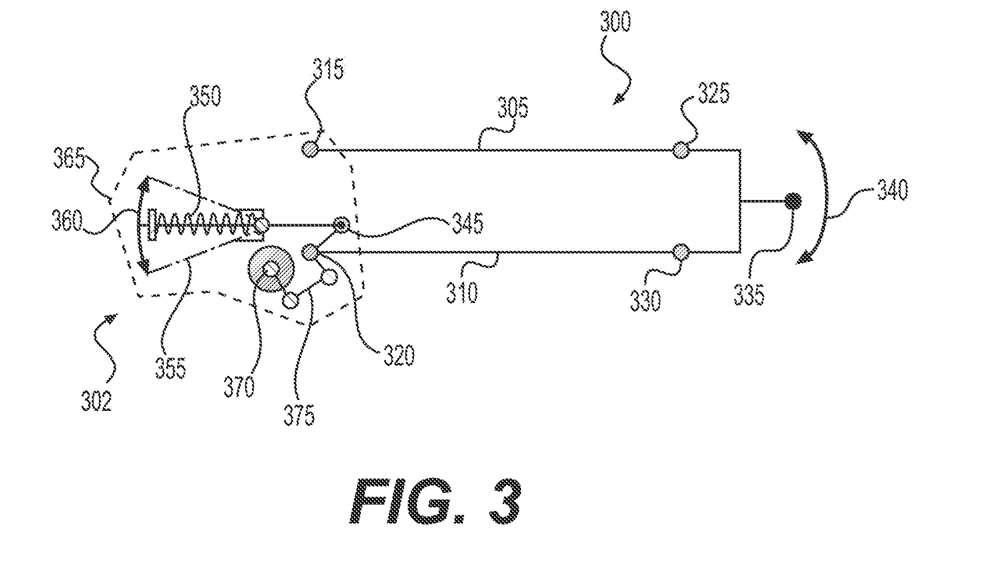
FIG. 3 shows a schematic illustration of a carrier arm and a swivel range of a torque compensation assembly according to an exemplary embodiment of the disclosure.

Reference is now made to FIG. 3 (with continued reference to FIGS. 1 and 2) which shows a schematic illustration of carrier arm 300 (which corresponds to the second carrier arm 130 in FIG. 1) according to an exemplary embodiment of the disclosure. FIG. 3 further shows a torque compensation assembly 302 which includes an elastically deformable energy storage device 350. The elastically deformable energy storage device 350 can be a compression spring, but is not limited thereto. Any other elastically deformable energy storage device such as a gas spring, etc. can also be used.

The carrier arm 300 in FIG. 3 is in a middle position, i.e., in a position in which the carrier arm extends essentially parallel to a floor (not shown). The carrier arm 300 includes a first carrier arm part 305 having a first connecting point 315 and a second connecting point 325, and a second carrier arm part 310 having a third connecting point 320 and a fourth connecting point 330, which together form a parallel kinematics. A load (such as the microscope head 155 shown in FIG. 1) can be mounted at load mounting point 335 via a suspension mechanism (not shown).

The first carrier arm part 305 is pivotable about the first connecting point 315 and the second carrier arm part 310 is pivotable about the third connecting point 320, thereby allowing the carrier arm 300 to be vertically swiveled together with the load mounted at the load mounting point 335, as indicated by arrows 340.

In order to significantly reduce the swivel range of the elastically deformable energy storage device 350, the position of the connecting point 345 of the elastically deformable energy storage device 350 relative to the first connecting point 315 and the third connecting point 320 is moved towards the third connecting point 320 and also in the direction of the fourth connecting point 330 (if compared with the position of connecting point 245 in FIG. 2).

This results in a shorter lever on the second carrier arm part 310 and also in a balancing error which varies depending on a rotation angle of the carrier arm 300 and depending on a weight of the objects mounted at the load mounting point 335. On the other hand, the swivel range 355 of the elastically deformable energy storage device 350 is significantly reduced in comparison with the swivel range 255 shown in FIG. 2. For example, if the carrier arm 300 is swiveled between an upper swivel position and a lower swivel position in a swivel range between zero degrees and sixty degrees, the elastically deformable energy storage device 350 has a swivel range 355 between zero and five degrees. As a result, the disturbance contour resulting from cover 365 can be significantly reduced in comparison with the disturbance contour resulting from cover 265 in FIG. 2.

The balancing error resulting from the replacement of the connecting point 345 of the elastically deformable energy storage device 350 is compensated by a compensation assembly which includes a motor 370 fixedly mounted at the third connecting point 320 on the second carrier arm part 310 via a coupling mechanism 375.

Figure 4A:
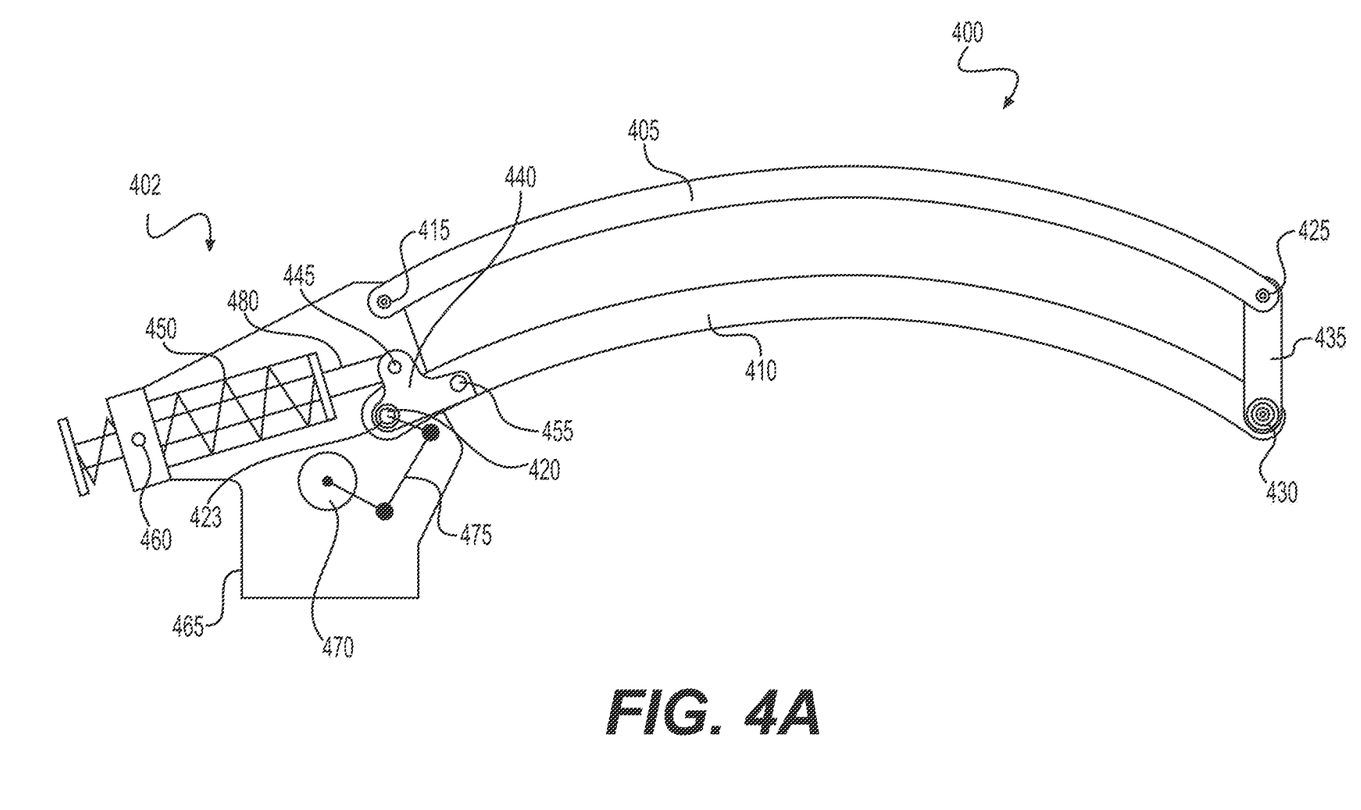
FIG. 4A shows a carrier arm in a middle swivel position according to a first exemplary embodiment of the disclosure.

Referring now to FIG. 4A, which shows a carrier arm 400 as part of a stand for a surgical microscope according to a first exemplary embodiment of the disclosure. The carrier arm 400 is shown in FIG. 4A in a middle swivel position.

As shown in FIG. 4A, the stand includes a first stand part 465. A first bearing 423 and a second bearing 460 are provided on the first stand part 465 and a shaft 420 is arranged in the first bearing 423. The first bearing 423 defines a rotation axis of the shaft 420.

A main support arm 410 (which correspond to the second carrier arm part 310 shown in FIG. 3) is fixedly connected to the shaft 420, is mounted on the first stand part 465 together with the shaft 420, and is pivotable about the rotation axis of the shaft 420. The main support arm 410 also includes a force transmission point 455.

The carrier arm 400 shown in FIG. 4A also includes secondary support arm 405. The main support arm 410 is pivotably mounted on the connection element 435 in bearing 430. A surgical microscope head (not shown) may be mounted on the connection element 435 via a suspension mechanism (not shown). The secondary support arm 405 is pivotably mounted on the first stand part 465 in bearing 415 and on the connection element 435 in bearing 425 to compensate a tilting torque occurring on the connection element 435.

Both the main support arm 410 and the secondary support arm 405 have a curved shape.

When the carrier arm 400 is swiveled from the middle swivel position shown in FIG. 4A to another swivel position, a dynamic torque and a static torque need to be compensated in order to permit a smooth and near-force-free movement. While the dynamic torque occurs when the carrier arm 400 is pivoted about the rotation axis defined by the shaft 420, the static load torque results from a gravitation force acting on the carrier arm 400 and on elements (such as the microscope head) mounted on carrier arm 400. To compensate the dynamic load torque and the static load torque, torque compensation assembly 402 is provided to apply a counter torque to the main support arm 410 to compensate the dynamic load torque and the static load torque.

As shown in FIG. 4A, a lever part 440 is mounted on the main support arm 410 at the force transmission point 455. The lever part 440 is arranged pivotably about the rotation axis of the shaft 420 and includes a bearing 445.

The torque compensation assembly 402 includes a first torque compensation assembly 450 and a second torque compensation assembly 470. The first torque compensation assembly 450 is mounted on the first stand part 465 in the bearing 460 pivotably within a swivel range. The first torque compensation assembly 450 further includes a rod 480 which is displaceable relative to the first stand part 465 and which is mounted on the lever part 440 in the bearing 445.

The position of the bearing 445 on the lever part 440 relative to the bearing 423 is a position at which a minimum swivel range of the first torque compensation assembly 450 about an axis defined by the bearing 460 is achieved. This swivel range is between zero degrees and five degrees. However, this positioning, which is intentionally different from the optimum position of the bearing 445 prevents the dynamic and static load torques from being entirely canceled out by the counter torque generated by the first torque compensation assembly 450 thereby causing a balancing error.

To compensate the balancing error, the second torque compensation assembly 470 generates an additional counter torque which is added to the counter torque generated by the first torque compensation assembly 450 and which results in the required smooth and near-force-free movement of the carrier arm 400 including any load arranged on the connection element 435. At the same time, the disturbance contour of the first stand part 465 and the space requirement for the first torque compensation assembly 450 are significantly reduced.

According to an exemplary embodiment of the disclosure, the second torque compensation assembly 470 is an electrical motor or an electrical motor with a gear. The electrical motor includes a motor shaft, and the motor shaft is either directly mounted on the shaft 420 or by a coupling mechanism 475.

As shown in FIG. 4A, bearings 423, 425, 430, and 415 form a parallelogram. The parallelogram defines a swivel range within which the carrier arm 400 is pivotable about the rotation axis defined by the shaft 420. This swivel range is between zero degrees and sixty degrees.

Figure 4B:
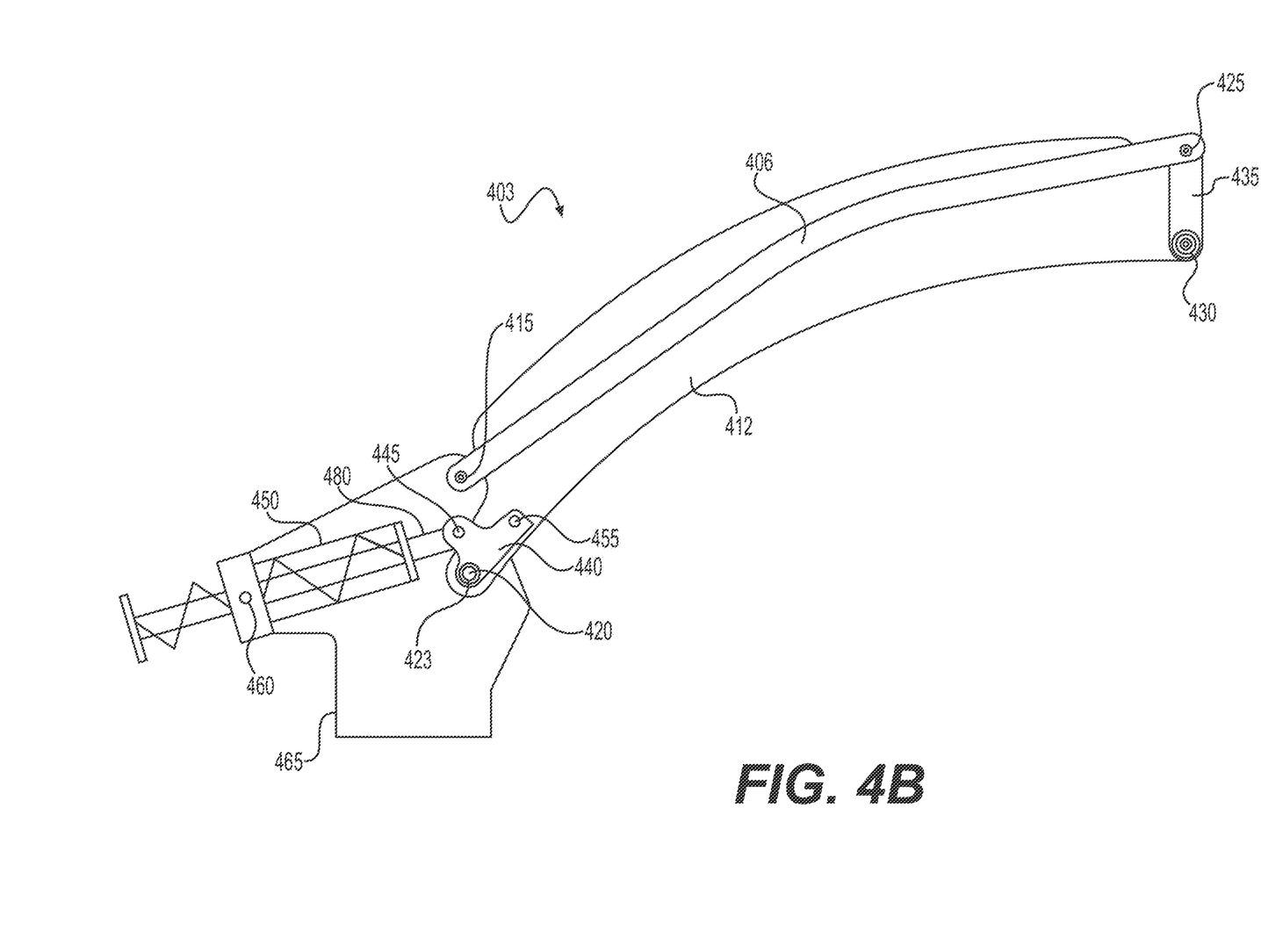
FIG. 4B shows a carrier arm in an upper swivel position according to a second exemplary embodiment of the disclosure.
Figure 4C:
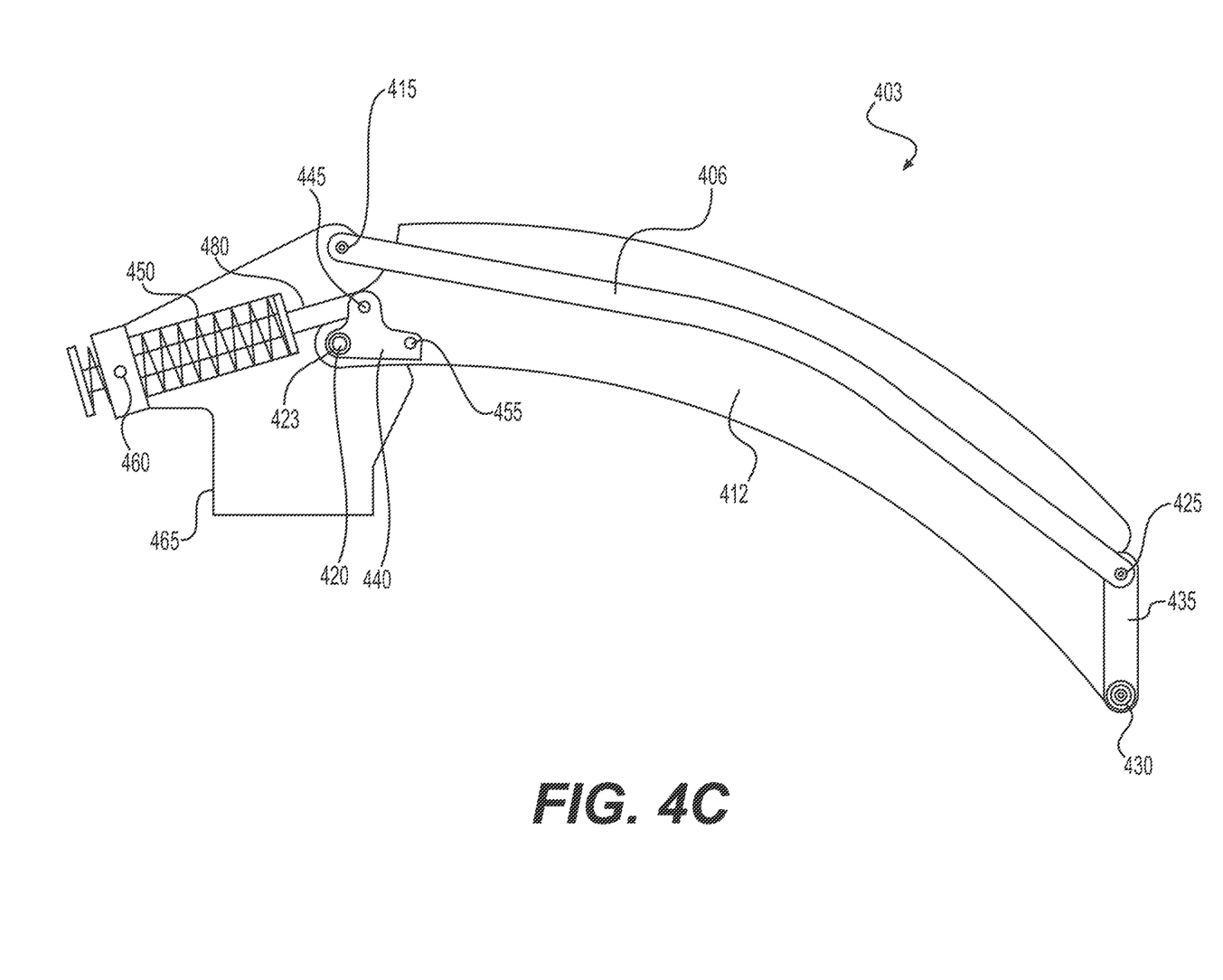
FIG. 4C shows a carrier arm in a lower swivel position according to the second exemplary embodiment of the disclosure.

FIGS. 4B and 4C show a carrier arm 403 in an upper swivel position and in a lower swivel position, respectively, according to a second exemplary embodiment of the disclosure. The second exemplary embodiment of the carrier arm differs from the first exemplary embodiment in that the secondary support arm 406 is arranged inside the main support arm 412.

Both the main support arm 406 and the secondary support arm 412 have a curved shape.

The remaining elements of the carrier arm 403 are the same elements as shown in FIG. 4A. In particular, although not shown in FIGS. 4B and 4C, the torque compensation assembly 402 in the second exemplary embodiment of the disclosure also includes the second torque compensation assembly 470 in addition to the first torque compensation assembly 450 to compensate the balancing error.

Figure 5:
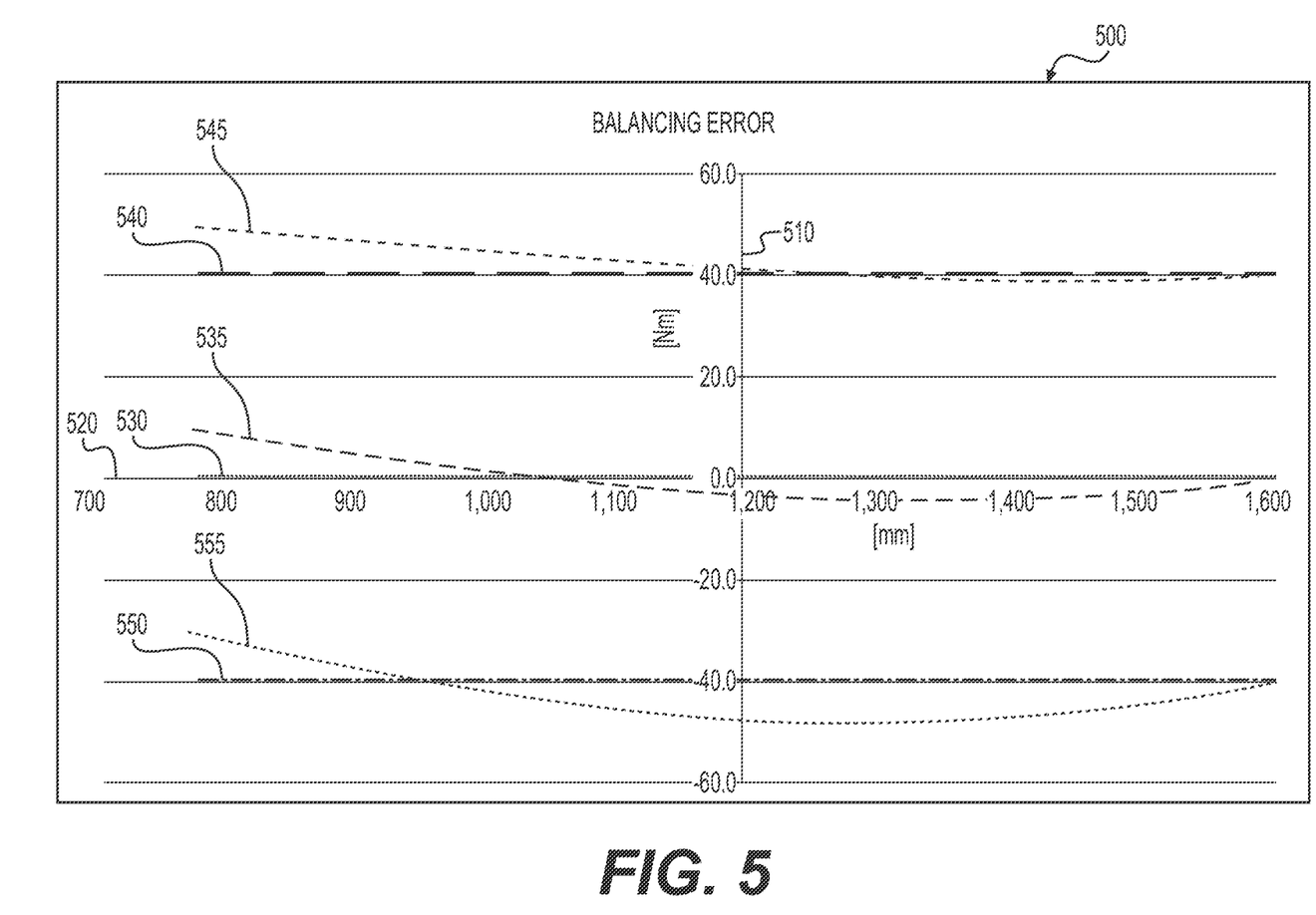
FIG. 5 shows a diagram illustrating a balancing error for different loads and depending on a vertical position of the microscope head of a surgical microscopy system according to an exemplary embodiment of the disclosure.

Reference is now made to FIG. 5 (with continued reference to FIGS. 4A to 4C). FIG. 5 shows a diagram 500 illustrating a balancing error that needs to be compensated by the second torque compensation assembly 470 for different loads and depending on a vertical position of the microscope head of a surgical microscopy system according to an exemplary embodiment of the disclosure.

Specifically, the diagram 500 includes axis 510, which represents a torque in Newton meters (Nm) and axis 520, which represents a height of the microscope head over ground in millimeters (mm).

Diagram curves 535, 545 and 555 show the balancing error as torque over the height of the microscope head over ground for different loads. More specifically, diagram curve 535 shows the balancing error in torque over the height of the microscope head over ground for a medium load, whereas diagram curves 545 and 555 show the balancing errors in torque over the height of the microscope head over ground for high and low loads, respectively. A high load means that a weight on the connecting element 435 is higher than the weight on the connecting element 435 for a medium or low load. Medium load means that the weight on the connecting element 435 is higher than the weight on the connecting element 435 for a low load and lower than the weight on the connecting element 435 for a high load. A low load means that the weight on the connecting element 435 is lower than the weight on the connecting element 435 for a medium or high load.

Diagram curves 540, 530, and 550 show torques to be compensated without any balancing error which could be achieve with a configuration as shown in FIG. 2 at the cost of a substantially larger disturbance contour.

As shown in FIG. 5, the balancing error over the height of the microscope head over ground follows non-linear functions that differ from one another for each load. The balancing error is determined by a sensor (not shown) and a control unit (not shown) controls the second torque compensation assembly 470 to apply a respective positive or negative torque to the main carrier arms 410 and 412, respectively.

Figure 6:
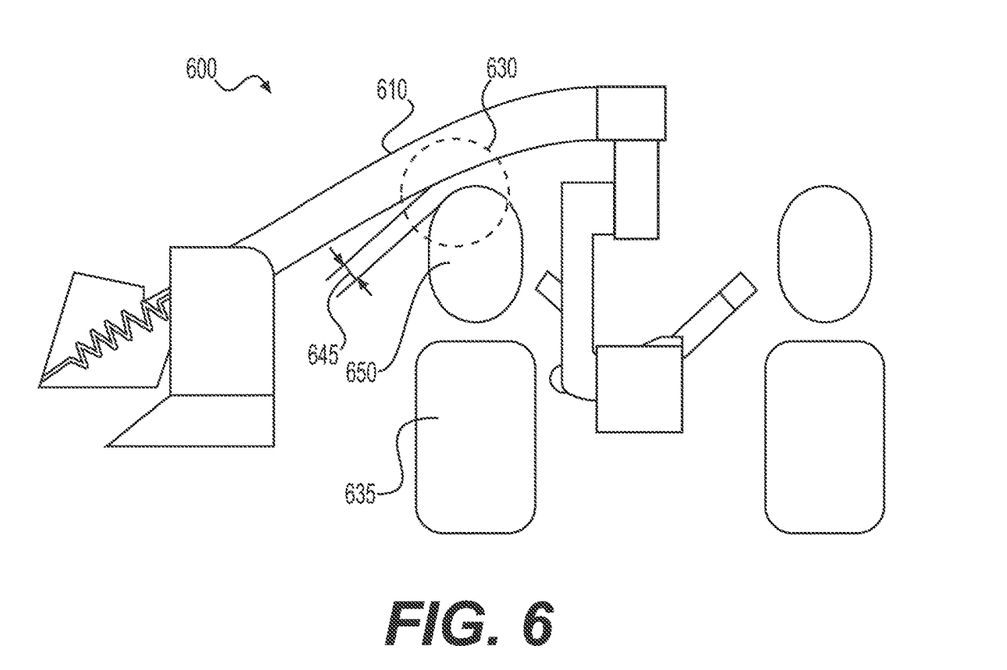
FIG. 6 shows surgical microscopy system with a small overhead clearance of a carrier arm known from the related art.

FIG. 6 shows surgical microscopy system 600 with a small overhead clearance 645 of a carrier arm 610 for personnel 635 standing under the carrier arm 610 known from to the related art. The small clearance 645 in the area 630 above the head 650 of the person 635 results from the relatively straight design and the swivel range of the carrier arm 610 in the related art.

Figure 7:
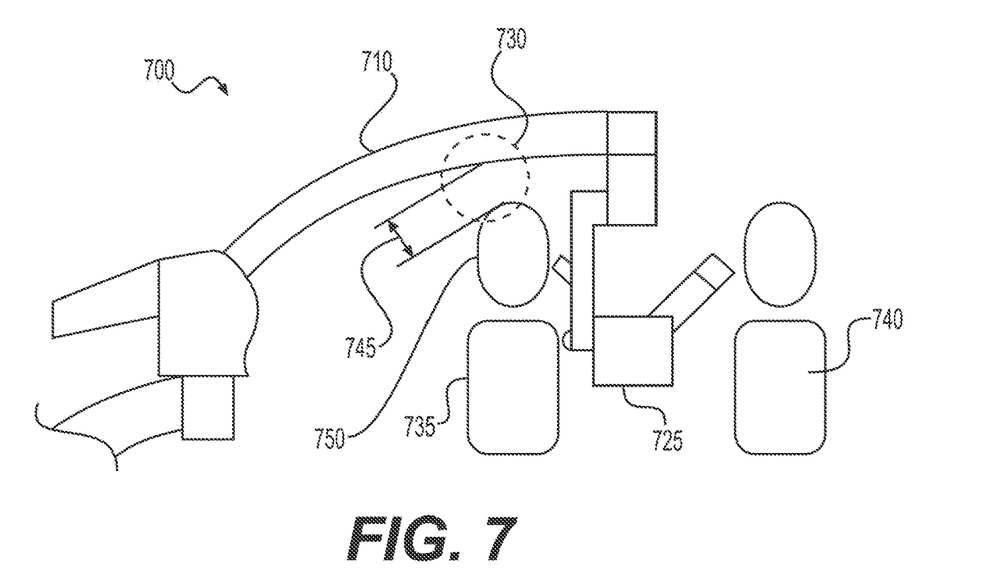
FIG. 7 shows a surgical microscopy system with an overhead clearance of a carrier arm according to an exemplary embodiment of the disclosure.

Reference is now made to FIG. 7 (with continued reference to FIGS. 4B and 4C). FIG. 7 shows a surgical microscopy system 700 with an overhead clearance 745 of carrier arm 710 according to an exemplary embodiment of the disclosure. As shown in FIG. 7, doctor(s) 735 and 740 and assistant(s) operate in positions facing toward each other, i.e., in positions on opposite sides of a patient (not shown). This is possible, e.g., by utilizing an optical beam divider (stereo bridge) and 2 tubes on the microscope head 725. As shown in FIG. 7, at least one person 735 must stand directly under the carrier arm 710. Therefore, a certain overhead clearance 745 in the area 730 between the carrier arm 710 and the head 750 of the person 735 standing directly under the carrier arm 710 needs to always be maintained.

A sufficient overhead clearance 735 even for teams of doctors with unfavorable size ratios needs to be maintained. For example, a doctor who is 2 meters tall should still ensure approximately 100 mm of overhead clearance to avoid unsterile contact. At the same time, the height of the stand is limited to between 1.90 meters and 2.00 meters due to the often low door clearance height in hospitals or entrances to the operating theatre, so that this free space can only be achieved by a favorable swivel range of the carrier arm 710 and an overhead clearance favoring contour. This contour can be optimally realized by a curved carrier arm as shown in FIGS. 4B and 4C.

In particular, closed hollow sections, such as the main support arm 412 are the ideal solution for such requirements due to the requirements for load-bearing capacity and torsional stiffness in the carrier arm 710. Variable curvature and torsional stiffness can be completely solved by a closed welding profile. In order to optimize costs while at the same time minimizing installation space requirements, a design made of sheet steel, in which the secondary support arm 406 is also guided inside, is ideal. As a result, the overhead clearance 745 of approximately 100 mm can always be guaranteed.

Figure 8:
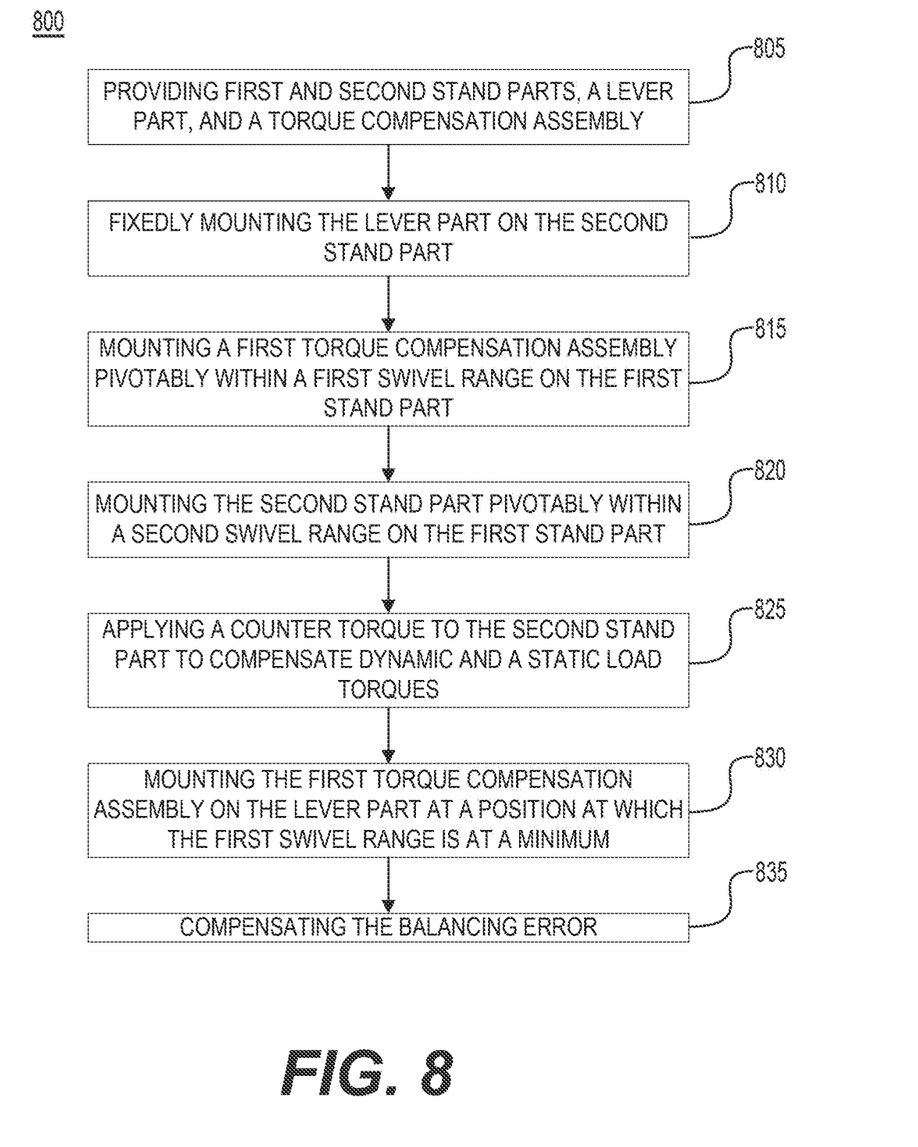
FIG. 8 shows a flow chart of a method for compensating a balancing error in a stand of a surgical microscope according to an exemplary embodiment of the disclosure.

Referring now to FIG. 8 (with continued reference to FIGS. 4A to 4C), a flow chart of method 800 for compensating a balancing error in a stand of a surgical microscope is shown. Method 800 begins at 805 at which a first stand part 465, a second stand part 410 or 412, a lever part 440, and a torque compensation assembly 402 are provided. The torque compensation assembly includes a first torque compensation assembly 450 and a second torque compensation assembly 470.

Method 800 continues to step 810 at which the lever part 440 is fixedly mounting on the second stand part 410 or 412. At 815, the first torque compensation assembly 450 is mounted pivotably within a first swivel range on the first stand part 465. The method 800 continues to step 820 at which the second stand part 410 or 412 is pivotably mounted within a second swivel range on the first stand part 465. At 825, a counter torque is applied to the second stand part 410 or 412 to compensate a dynamic load torque occurring when the second stand part 410 or 412 is pivoted relative to the first stand part 465 and a static load torque resulting from a gravitation force acting on the second stand part 410 or 412 and on elements mounted on the second stand part 410 or 412.

At 830, the first torque compensation assembly 450 is mounted on the lever part 440 at a position at which the first swivel range is at a minimum thereby causing a balancing error preventing the first portion of the counter torque to cancel out the entire load torque (including the dynamic and the static load torque). The method 800 ends at 835 at which the balancing error is compensated by the second portion of the counter torque. The counter torque includes a first portion and a second portion, the first portion is applied by the first torque compensation assembly 450 and the second portion is applied by the second torque compensation assembly 470.

It is understood that the foregoing description is that of the exemplary embodiments of the invention and that various changes and modifications may be made thereto without departing from the spirit and scope of the invention as defined in the appended claims.

What is claimed is:

1. An apparatus for compensating a balancing error in a stand for a surgical microscope, the apparatus comprising:
   a first stand part including a first bearing and a second bearing;
   a shaft arranged in the first bearing and defining a rotation axis;
   a second stand part fixedly connected to the shaft, mounted on the first stand part together with the shaft pivotably about the rotation axis, and including a force transmission point;
   a lever part mounted on the second stand part at the force transmission point, arranged pivotably about the rotation axis, and including a third bearing;
   a torque compensation assembly applying a counter torque to the second stand part to compensate a load torque including a dynamic load torque occurring when the second stand part is pivoted about the rotation axis and a static load torque resulting from a gravitation force acting on the second stand part and on elements mounted on the second stand part;
   the torque compensation assembly includes a first torque compensation assembly and a second torque compensation assembly,
   the rotation axis is a first rotation axis,
   the second bearing defines a second rotation axis,
   the first torque compensation assembly is mounted on the first stand part in the second bearing pivotably about the second rotation axis within a first swivel range,
   the first torque compensation assembly includes a rod displaceable relative to the first stand part and mounted on the lever part in the third bearing, and
   the second torque compensation assembly is fixedly mounted on the shaft.

2. The apparatus of claim 1, wherein:
   the counter torque includes a first portion and a second portion,
   the first torque compensation assembly applies the first portion of the counter torque to the second stand part thereby partially counteracting the load torque,
   the third bearing is arranged on the lever part at a position relative to the first bearing at which the first swivel range is a minimum swivel range thereby causing the balancing error preventing the first portion of the counter torque to cancel out the load torque,
   the second torque compensation assembly applies the second portion of the counter torque to the second stand part, and
   the second portion of the counter torque compensates the balancing error and an offset between different loads.

3. The apparatus of claim 2, wherein the balancing error varies depending on a rotation angle between the first stand part and the second stand part when the second stand part is pivoted about the first rotation axis and depending on a weight of objects mounted on the second stand part.

4. The apparatus of claim 3, wherein the objects mounted on the second stand part include a surgical microscope head and a suspension mechanism.

5. The apparatus of claim 2, wherein the first torque compensation assembly pivots within the minimum swivel range between zero degrees and five degrees.

6. The apparatus of claim 1, wherein the first torque compensation assembly is a compression spring.

7. The apparatus of claim 1, wherein the second torque compensation assembly is an electrical motor or an electrical motor with a gear.

8. The apparatus of claim 7, wherein the electrical motor includes a motor shaft, and
   the motor shaft is mounted on the shaft by a coupling mechanism.

9. The apparatus of claim 1, further comprising:
   a connection element including a fourth bearing and a fifth bearing, wherein:
   the second stand part includes a main support arm and a secondary support arm,
   the first stand part includes a sixth bearing,
   the main support arm is pivotably mounted on the connection element in the fifth bearing, and
   the secondary support arm is pivotably mounted on the first stand part in the sixth bearing and on the connection element in the fourth bearing to compensate a tilting torque occurring on the connection element.

10. The apparatus of claim 9, wherein:
the secondary support arm is arranged inside the main support arm,
each of the main support arm and the secondary support arm has a curved shape.

11. The apparatus of claim 9, wherein:
the first, fourth, fifth, and sixth bearings form a parallelogram,
the parallelogram defines a second swivel range within which the second stand part is pivotable about the rotation axis, and
the second swivel range is between zero degrees and sixty degrees.

12. A surgical microscopy system for compensating a balancing error in a stand for a surgical microscope, the surgical microscopy system comprising:
the stand including:
a first stand part including a first bearing and a second bearing;
a shaft arranged in the first bearing and defining a rotation axis;
a second stand part fixedly connected to the shaft, mounted on the first stand part together with the shaft pivotably about the rotation axis, and including a force transmission point;
a lever part mounted on the second stand part at the force transmission point, arranged pivotably about the rotation axis, and including a third bearing;
a torque compensation assembly applying a counter torque to the second stand part to compensate a load torque;
a connection element including a fourth bearing and a fifth bearing;
the second stand part including a main support arm and a secondary support arm,
the second stand part including a sixth bearing;
the secondary support arm being pivotably mounted on the second stand part in the sixth bearing and on the connection element in the fourth bearing, and
the main support arm being pivotably mounted on the connection element in the fifth bearing; and
a surgical microscope head mounted on the connection element via a suspension mechanism; and
the load torque occurring when the second stand part is pivoted together with the surgical microscope head about the rotation axis.

13. The surgical microscopy system of claim 12, wherein the secondary support arm is arranged inside the main support arm,
each of the main support arm and the secondary support arm has a curved shape, and
the curved shape of the main support arm and the secondary support arm provides an overhead clearance between the second stand part and a head of a person standing underneath the second stand part of at least 100 millimeters.

14. The surgical microscopy system of claim 12, wherein:
the torque compensation assembly includes a first torque compensation assembly and a second torque compensation assembly,
the rotation axis is a first rotation axis,
the second bearing defines a second rotation axis,
the first torque compensation assembly is mounted on the first stand part in the second bearing pivotably about the second rotation axis within a first swivel range,
the first torque compensation assembly includes a rod displaceable relative to the first stand part and mounted on the lever part in the third bearing, and
the second torque compensation assembly is fixedly mounted on the shaft.

15. The surgical microscopy system of claim 14, wherein:
the counter torque includes a first portion and a second portion,
the first torque compensation assembly applies the first portion of the counter torque to the second stand part thereby partially counteracting the load torque,
the third bearing is arranged on the lever part at a position relative to the first bearing at which the first swivel range is a minimum swivel range thereby causing the balancing error preventing the first portion of the counter torque to cancel out the load torque,
the second torque compensation assembly applies the second portion of the counter torque to the second stand part, and
the second portion of the counter torque compensates the balancing error and an offset between different loads.

16. The surgical microscopy system of claim 15, wherein the balancing error varies depending on a rotation angle between the first stand part and the second stand part when the second stand part is pivoted about the first rotation axis and depending on a weight of objects mounted on the second stand part.

17. The surgical microscopy system of claim 16, wherein the objects mounted on the second stand part include the surgical microscope head and a suspension mechanism.

18. A method for compensating a balancing error in a stand of a surgical microscope, the method comprising:
providing a first stand part, a second stand part, a lever part, and a torque compensation assembly, the torque compensation assembly including a first torque compensation assembly and a second torque compensation assembly of the stand;
fixedly mounting the lever part on the second stand part;
mounting the first torque compensation assembly pivotably within a first swivel range on the first stand part;
mounting the second stand part pivotably within a second swivel range on the first stand part;
applying a counter torque to the second stand part to compensate a dynamic load torque occurring when the second stand part is pivoted relative to the first stand part and a static load torque resulting from a gravitation force acting on the second stand part and on elements mounted on the second stand part, the counter torque including a first portion and a second portion, the first portion being applied by the first torque compensation assembly and the second portion being applied by the second torque compensation assembly;
mounting the first torque compensation assembly on the lever part at a position at which the first swivel range is a minimum swivel range thereby causing the balancing error preventing the first portion of the counter torque to cancel out the load torque; and
compensating the balancing error by the second portion of the counter torque.

19. The method of claim 18, further comprising:
pivoting the first torque compensation assembly within the minimum swivel range between zero degrees and five degrees.

* * * * *